United States Patent [19]

Kolaczkowski et al.

[11] Patent Number: 5,319,105

[45] Date of Patent: Jun. 7, 1994

[54] DERIVATIVES AND ANOLOGS OF MONOETHYLGLYCINEXYLIDIDE

[75] Inventors: Lawrence Kolaczkowski, Gurnee; Mark Littlefield, Arlington Heights, both of Ill.

[73] Assignee: Abbott Laboratories, Abbott Park, Ill.

[21] Appl. No.: 820,727

[22] Filed: Jan. 14, 1992

Related U.S. Application Data

[62] Division of Ser. No. 455,467, Dec. 22, 1989, Pat. No. 5,099,000.

[51] Int. Cl.$^5$ .......................................... C07D 493/10
[52] U.S. Cl. ...................................................... 549/223
[58] Field of Search ......................................... 549/223

[56] References Cited

U.S. PATENT DOCUMENTS

| | | | |
|---|---|---|---|
| 4,510,251 | 4/1985 | Kirkemo et al. | 436/536 |
| 4,593,089 | 6/1986 | Wang et al. | 536/13.6 |
| 4,614,823 | 9/1986 | Kirkemo et al. | 544/300 |
| 4,668,640 | 5/1987 | Wang et al. | 436/536 |
| 5,099,000 | 3/1992 | Kolaczkowski et al. | 530/363 |

OTHER PUBLICATIONS

J. Clin. Chem. Clin. Biochem. vol. 25, 1987, pp. 845–853 "Monoethylglycinexylidide Formation Kinetics: A Novel Approach to Assessment of Liver Function".

*Primary Examiner*—Richard L. Raymond
*Attorney, Agent, or Firm*—Gregory W. Steele; Thomas M. Breininger

[57] ABSTRACT

A substituted monoethylglycinexylidide or analogue is disclosed. The xylidide or analogue has the structure of FIG. 1 of the attached drawings where M is $CH_2NHCH_2CH_3$, $CH_2CH_2CH_2CH_3$ or $CH_2OCH_2CH_3$, one of $Y^1$ and $Y^2$ is H and the other is a protein or a fluorescein moiety chemically bonded to the glycinexylidide or analogue moiety. Also disclosed is a method for carrying out immunoassays for MEGX, which has the structure of FIG. 3 of the attached drawings. The method for carrying out immunoassays involves using the foregoing compounds as tracers and immunogens.

4 Claims, 3 Drawing Sheets

DERIVATIVES AND ANOLOGS OF MONOETHYLGLYCINEXYLIDIDE

This is a division of application Ser. No. 07/455,467, filed Dec. 22, 1989, now U.S. Pat. No. 5,099,000.

FIELD OF THE INVENTION

This invention relates to derivatives and analogues of monoethylglycinexylidide ("MEGX") and their production and use. The derivatives and analogues, which have the structure of FIG. 1 of the attached drawings, are useful as tracers and immunogens in carrying out immunoassays for MEGX, which has the structure of FIG. 3 of the attached drawings.

BACKGROUND OF THE INVENTION

The MEGX derivatives and analogues of the invention are believed to be new compounds.

It is known that fluorescence polarization immunoassays can be used for determining levels of biologically interesting moieties such as valproic acid in serum, plasma, urine and the like, being disclosed, for example, in U.S. Pat. No. 4,593,089, granted to Wang et al. on Jun. 3, 1986. The patent discloses, by way of example, a method for determining levels of valproic acid in samples which involves mixing with the samples a biologically acceptable salt of 2-ethyl-5-aminopentanoic acid-5-[(4,6-dichlorotriazin-2-yl)-amino]-fluorescein conjugate as a tracer, and sheep antiserum to valproic acid as an antibody which recognizes both the valproic acid and the tracer. The valproic acid (a ligand) and the tracer both form complexes with the antibody; the concentrations of tracer and of antibody are both kept constant so that the ratio of ligand-antibody complex to tracer-antibody complex that is formed is directly proportional to the amount of ligand present in the sample. Therefore, upon exciting the mixture with fluorescent light and measuring the polarization of the fluorescence emitted by the tracer and the tracer-antibody complex, it is possible to determine the amount of ligand in the sample by fluorescence polarization techniques.

Fluorescence polarization techniques, as is disclosed in the aforesaid Wang et al. patent, involve determining the polarization of fluorescence of several samples, some known and some unknown, preparing a standard curve showing polarization as a function of concentration from the data for the known samples, and then using the standard curve to determine the concentration of the unknown samples from the measured polarization.

It is also known that certain aminomethylfluoresceins can be used as tracers in using fluorescence polarization techniques to determine levels of biologically interesting moieties such as valproic acid in serum, plasma, urine and the like. By way of example, U.S. Pat. No. 4,510,251, granted to Kirkemo et al. on Apr. 9, 1985, discloses a method for determining levels of estriol and of cortisol in samples which involves mixing with the samples estriol carboxymethyloxime aminomethylfluorescein and cortisol-3-carboxymethyloxime aminomethylfluorescein, respectively, as tracers, and antiserum raised against estriol and antiserum raised against cortisol, respectively, as antibodies, and then determining the amount of tracer-antibody conjugate by fluorescence polarization techniques.

It has also been disclosed (Oellerich et al.: "Monoethylglycinexylidide formation and liver function, J.Clin.Chem Biochem./Vol. 25, 1987/No. 12) that fluorescence polarization immunoassay techniques can be used to determine MEGX in serum and in urine, and that measurements of the content of MEGX in serum from venus blood following an intravenous lidocaine bolus (which has the structure of FIG. 2 of the attached drawing) injection can provide a reliable indication of liver function. The reference does not disclose the identity of the reagents used for the immunoassay, stating only that they were provided for investigational use by Abbott Laboratories, the assignee of the subject invention.

BRIEF DESCRIPTION OF THE PRESENT INVENTION

The present invention is based upon the discovery of a glycinexylidide or analogue having the structure of FIG. 1 of the drawings where one of $Y^1$ and $Y^2$ is H, the other includes a fluorescein moiety or a bovine serum albumin moiety that is chemically bonded to the glycinexylidide or analogue and M is $CH_2NHCH_2CH_3$. The invention is also based upon the further discoveries that when one of $Y^1$ and $Y^2$ includes a fluorescein moiety the compound is useful as a tracer in carrying out a fluorescence polarization immunoassay for MEGX in biological fluids such as serum, urine, whole blood, and the like and when one of $Y^1$ and $Y^2$ includes a bovine serum albumin moiety, the compound is useful as an immunogen in carrying out a fluorescence polarization immunoassay for MEGX in biological fluids such as serum, urine, whole blood, and the like.

The invention is also based upon the discovery that the foregoing compounds, in suitable solutions, especially buffered aqueous solutions at a pH in the range of about 1.5 to about 2.1, are stable for extended periods of time, while the compounds themselves and solutions thereof in alcohols typically employed to store such compounds, such as ethanol, methanol, and the like, are stable for only short periods of time, so short that it is necessary to synthesize and purify the compounds just before they are used to conduct an immunoassay.

DESCRIPTION OF THE PREFERRED EMBODIMENT

Figure 1:
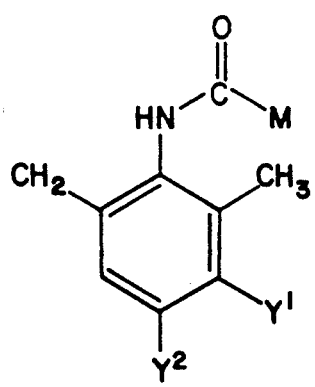
Figure 2:
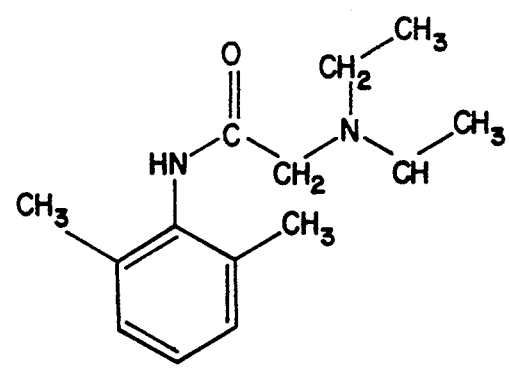
Figure 3:
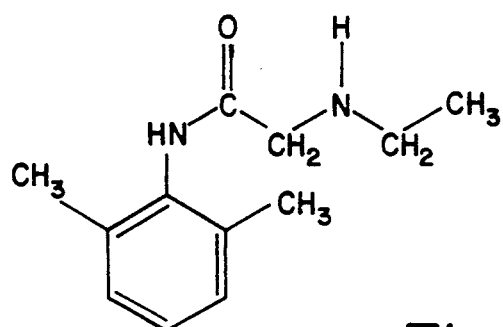

The invention will be more fully understood from the following examples, number 1 of which constitutes the best mode presently contemplated by the inventors, but the examples are presented solely for the purpose of illustration, and are not to be construed as limiting.

As used herein, and in the appended claims, the terms "percent" and "parts" refer to percent and parts by weight, unless otherwise indicated; g means gram or grams; mg means milligram or milligrams; ng means nanogram or nanograms; cm means centimeter or centimeters; mm means millimeter or millimeters; l means liter or liters; μl means microliter or microliters; $m/_o$ means mole percent, and equals 100 times the number of moles of the constituent designated in a composition divided by the total number of moles in the composition; $v/_v$ means percent by volume; M means molar and equals the number of moles of a solute in 1 liter of a solution; N means normal, and equals the number of equivalents of a solute in 1 liter of solution; psi means pounds per square inch; and MPa means $10^6$ Pascals. All temperatures are in ° C., unless otherwise indicated.

Example 1, below, describes the synthesis of 3-amino-t-BOC-monoethylglycinexylidide ("3-amino-N-t-BOC-MEGX," a compound having the structure of FIG. 4 of the drawings), from 2,6-dimethyl aniline, and then describes the synthesis from 3-amino-N-t-BOC-MEGX of one of the foregoing tracers (structure of FIG. 1 of the drawings where $Y^2$ is H, $Y^1$ includes a fluorescein moiety which has the structure of FIG. 6 of the drawings and M is $CH_2NHCH_2CH_3$) and of one of the foregoing immunogens (structure of FIG. 1 of the drawings where $Y^2$ is H, $Y^1$ includes a bovine serum albumin moiety that is chemically bonded to the glycinexylidide as subsequently discussed in more detail, and M is $CH_2NHCH_2CH_3$).

EXAMPLE 1

N-acetyl-2,6-dimethyl aniline was first produced from 60 ml acetic anhydride, 20 ml glacial acetic acid and 50 ml 2,6-dimethyl aniline. The acetic anhydride and the acetic acid were mixed, and the dimethyl aniline was added dropwise to the mixture. The resulting mixture was heated on an oil bath to 120° and was maintained at 120° for one hour. The reaction products were then cast onto 250 ml crushed ice. The product, a beige solid, was collected by filtration, air dried, and then recrystallized from absolute ethanol, yielding 36 g white crystalline solid.

N-acetyl-3-nitro-2,6-dimethyl aniline was then produced from 34.75 g N-acetyl-2,6-dimethyl aniline and 12.2 ml fuming nitric acid dissolved in 35 ml $50^v/_v$ glacial acetic acid in concentrated sulfuric acid. The N-acetyl-2,6-dimethyl aniline was dissolved in 120 ml glacial acetic acid; concentrated sulfuric acid (105 ml) was added; and the mixture was cooled to room temperature of about 20° with an ice bath. The fuming nitric acid solution was added dropwise and cooling with the ice bath was used to keep the reaction temperature $\leq 45°$. The ice bath was removed after the fuming nitric acid addition was complete. The reaction mixture was stirred for about 16 hours at room temperature and was cast onto 400 ml ice. A solid which precipitated was recovered by suction filtration, dried, and recrystallized from $75^v/_v$ ethanol in water, yielding 33.76 g pale yellow needles. Concentration of the mother liquors yielded another 3.91 g powdery beige solid.

A 35.14 g portion of the N-acetyl-3-nitro-2,6-dimethyl aniline was then hydrolyzed to 3-nitro-2,6-dimethyl aniline. The N-aoetyl-3-nitro-2,6-dimethyl aniline was dissolved in 165 ml concentrated sulfuric acid to which 12 ml water had been added. The reaction mixture was then heated on a 120° oil bath for $\approx 2$ hours until an aliquot removed therefrom and quenched with water no longer yielded a precipitate. The reaction mixture was then cooled to room temperature and cast onto 500 ml ice. After the ice melted, solids were filtered from the liquid and the filtrate was neutralized with a 50 percent aqueous potassium hydroxide solution. The solid which resulted was collected by suction filtration, air dried, and heated in hexane containing $25^v/_v$ benzene. The solution which resulted was filtered to remove a small amount of insoluble material which remained, and was then cooled to room temperature. Suction filtration of the resultant solid yielded 28.0 g of the product, a bright yellow powdery solid.

N-(2-chloroacetyl)-3-Nitro-2,6-dimethyl aniline was made from 4.21 g pyridine in 200 ml dry benzene, 7.84 g 3-nitro-2,6-dimethyl aniline and 5.96 g chloroacetyl chloride in 25 ml dry benzene. The 3-nitro-2,6-dimethyl aniline was added to the pyridine solution, and the chloroacetyl chloride was then added dropwise. The reaction mixture was stirred at room temperature for one hour, and solids which formed were separated from the liquid by filtration. The filter cake was washed with 50 ml 0.1N HCl, and the solid which remained was recrystallized from ethanol containing $15^v/_v$ water, yielding 9.46 g of the product, colorless needles.

To produce 3-nitro-monoethylgylcinexylidide ("3-nitro-MEGX"), a reaction vessel equipped with a dry ice/acetone condenser was charged with 9.20 g N-(2-chloroacetyl)-3-Nitro-2,6-dimethyl aniline and 10 ml ethyl amine. The reaction mixture was stirred at room temperature for 1 hour, and was then concentrated by rotary evaporation. The crude product which resulted was dissolved in methylene chloride. The methylene chloride solution was washed with water and brine and was then dried on sodium sulfate. Solids were filtered from the dried solution, and the filtrate was subjected to rotary evaporation, which yielded 8.5 g crude product, a brown oil.

To produce 3-nitro-t-BOC-monoethylglycinexylidide ("3-nitro-t-BOC-MEGX;" the compound has the structure of FIG. 5 of the attached drawings), a mixture of 9.115 g crude 3-nitro-MEGX (the brown oil produced as described in the preceding paragraph) and 4.03 g triethyl amine was dissolved in 100 ml dry dimethyl formamide; the solution was cooled to 0° on an ice bath and a 9.32 g addition of di-t-butyl dicarbonate was made thereto. The resulting reaction mixture was allowed to stand on the ice bath, with stirring, for about 16 hours, during which time the ice in the bath melted. The reaction mixture was concentrated by rotary evaporation, diluted with 200 ml 0.1N HCl, and extracted three times with ethyl acetate. The three ethyl acetate extracts were combined, washed with water and brine, and dried with sodium sulfate. Solids were filtered from the dried extracts and solvent was removed from the filtrate, leaving a gummy solid which was dissolved in a small amount of solvent composed of hexanes and $30^v/_v$ ethyl acetate and purified by flash chromatography. The yield was 9.8 g of a viscous oil which solidified after standing.

A 100 mg portion of the crude 3-nitro-t-BOC-MEGX produced as described in the preceding paragraph was dissolved in 30 ml absolute ethanol and reduced to 3-amino-t-BOC-MEGX, using 10 mg platinum oxide as a catalyst. A solution of the 3-nitro-t-BOC-MEGX in the ethanol and the platinum oxide were placed in a large Parr bottle. The bottle was alternately evacuated and then pressurized with hydrogen three times, and was then pressurized to 50 psig with hydrogen and placed on a shaker. The pressure was released after one hour of shaking, and the catalyst was filtered from the reaction mixture and washed with absolute ethanol. The ethanol filtrate from the catalyst washing was combined with the reaction mixture filtrate and the combined organic phase was concentrated by rotary evaporation, yielding 85 mg product, a pleasant smelling tan oil which solidified upon standing.

Figure 6:
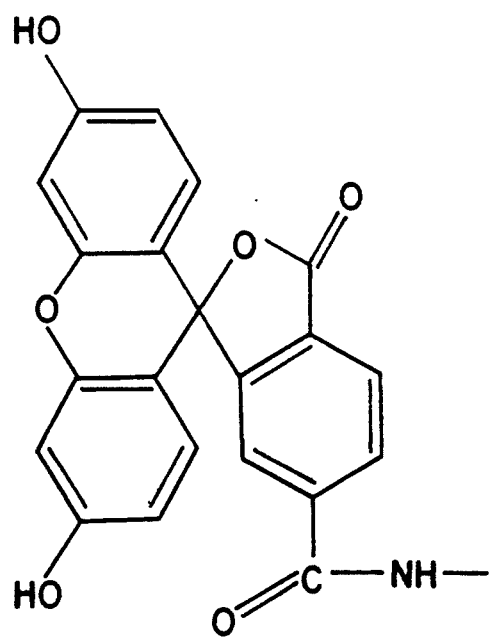

A tracer having the structure of FIG. 1 of the attached drawings where $Y^1$ is a fluorescein moiety having the structure of FIG. 6 of the attached drawings, $Y^2$ is H and M is $CH_2NHCH_2CH_3$ was produced from a solution of 19 mg 6-carboxy fluorescein in 250 μl dry dimethyl formamide, 23.2 mg isobutyl chloroformate, 17.4 mg triethyl amine and a solution of 11.1 mg 3-amino-t-BOC-monoethylglycinexylidide dissolved in 125 μl of dr formamide. The 6-carboxy fluorescein solution was cooled to 0°, using an ice bath; the isobutyl chloroformate was then added to the fluorescein solution, followed by the triethyl amine. After stirring at 0° for 150 minutes, the 3-amino-t-BOC-monoethylglycinexylidide solution was added, the ice bath was removed and the reaction mixture was stirred for about 16 hours, during which time it warmed to and was allowed to remain at room temperature. A 250 µl addition of methanol was then made, followed by a 50 µl addition of water and a 50 µl addition of saturated ammonium hydroxide. The reaction mixture was stirred for 45 minutes, and solvent was removed by high vacuum rotary evaporation, leaving an oil which was placed on a 0.5 mm × 20 cm × 20cm silica gel thick layer plate and developed using methylene chloride containing 20$^v/_v$ methanol. The appropriate band was cut from the plate and eluted with methanol. After solvent removal the solid which remained was dissolved in 4 ml methylene chloride containing 20 $^v/_v$ trifluoroacetic acid and stirred at room temperature for 1 hour. A 5 ml addition of methanol was made and, after stirring for 15 minutes, all volatiles were removed by rotary evaporation. The solid which remained was dissolved in a minimal amount of methanol and placed on a 0.5 mm × 20 cm × 20 cm silica gel thick layer plate. After the solvent evaporated the plate was developed with methylene chloride containing 20 $^v/_v$ methanol. The appropriate band was cut from the plate and the MEGX tracer was eluted from the silica gel with methanol. The solvent was immediately removed by rotary evaporation and the solid tracer which remained was stored in a freezer until needed.

A 300 mg portion of 3-amino-t-BOC-monoethylglycinexylidide was dissolved in 4 ml methylene chloride containing 25$^v/_v$ trifluoroacetic acid and stirred at room temperature for 30 minutes to produce 3-aminomonoethylglycinexylidide. A 5 ml addition of methanol was then made to the reaction mixture and, after stirring for an additional 15 minutes, all volatiles were removed by rotary evaporation, leaving a white powdery solid which was adsorbed onto silica gel, placed on a small flash column, and eluted with 300 ml methylene chloride containing 20$^v/_v$ methanol. Appropriate fractions were collected and evaporated to dryness, yielding 190 mg product, a beige colored oil which crystallized on standing.

An immunogen having the structure of FIG. 1 of the attached drawings where $Y^1$ includes a bovine serum albumin moiety chemically bonded to the monoethylglycinexylidide, $Y^2$ is H, and M is $CH_2NHCH_2CH_3$ was produced from 75 mg 3-aminomonoethylglycinexylidide, 23.4 mg sodium nitrite and 282 mg bovine serum albumin dissolved in 3 ml distilled water and adjusted to pH with 1N NaOH solution. The 3-aminomonoethylglycinexylidide was dissolved, with stirring, in 1.0 ml 1N hydrochloric acid on an ice bath and the sodium nitrite was added slowly to the resulting solution The solution was kept on the ice bath, with stirring, during the sodium nitrite addition and for about 30 minutes after the addition was complete, at which time the solution tested positive for the diazonium ion, indicating that the 3-amino-monoethylglycinexylidide in the solution had been diazotized. The diazonium solution was then added dropwise, with stirring, to the bovine serum albumin solution; during addition of the diazonium solution, pH of the reaction mixture was monitored, and additions of 1N NaOH were made as required to keep the pH between 10.8 and 11.2. The reaction mixture was stirred for an hour after addition of the diazonium solution was complete. Additions of 1N hydrochloric acid were made to the reaction mixture to adjust the pH thereof to 8.0, and the MEGX immunogen therein was purified by column chromatography (using sephadox G-50-300 that had been swelled with phosphate-buffered saline solution) and the immunogen fractions were collected and stored at 2°-8°.

Figure 7:
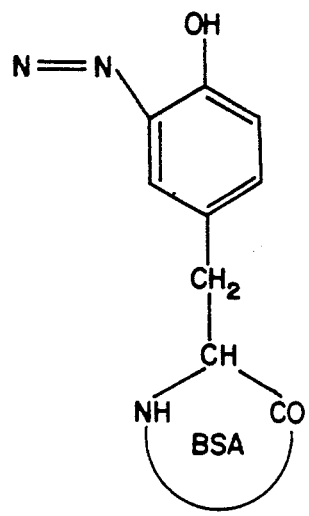

It has been found that the coupling reaction which produces the immunogen in the procedure described in the preceding paragraph occurs preferentially with tyrosine units (p-$HOC_6H_4CH_2CH(NH_2)COOH$) on the surface of the bovine serum albumin, in which case the immunogen has the structure of FIG. 1 of the attached drawings where $Y^2$ is H, M is $CH_2NHCH_2CH_3$, and $Y^1$ has the structure of FIG. 7 of the drawings.

Example 2, below, describes the synthesis of a compound which is herein named as "4-amino-N-t-BOC-MEGX" (a position isomer of the compound of FIG. 4 of the drawings where $NH_2$ is in the 4- position) from 2,6-dimethyl aniline, and then describes the synthesis from 4-amino-N-t-BOC-MEGX of one of the foregoing tracers (structure of FIG. 1 of the drawings where $Y^1$ is H, $Y^2$ is a fluorescein moiety having the structure of FIG. 6 of the drawings, and M is $CH_2NHCH_2CH_3$) and of one of the foregoing immunogens (structure of FIG. 1 of the drawings where $Y^1$ is H, $Y^2$ includes a bovine serum albumin moiety chemically bonded to the monoethylglycinexylidide and M is $CH_2NHCH_2CH_3$; as is explained above, when the coupling reaction which produces the immunogen occurs with tyrosine units (p-$HOC_6H_4CH_2CH(NH_2)COOH$) on the surface of the bovine serum albumin, $Y^2$ has the structure of FIG. 7 of the drawings).

EXAMPLE 2

N-toluenesulfonyl-2,6-dimethyl aniline was first produced from 29.72 g p-toluenesulfonyl chloride and 18 g 2,6-dimethyl aniline. The toluenesulfonyl chloride, the dimethyl aniline and 2 ml dry pyridine were heated on a 100. bath for 1 hour, and the reaction mixture was cast onto 250 ml ice. Solids which precipitated were collected by suction filtration, and were then recrystallized from absolute ethanol, yielding 38.34 g colorless needles.

N-toluenesulfonyl-4-nitro-2,6-dimethyl aniline was then produced from 1.375 g N-toluenesulfonyl-2,6-dimethyl aniline, which was mixed with 1.3 ml nitric acid, 10 ml glacial acetic acid and 40 mg sodium nitrite in 10 ml water. The mixture was then heated to reflux (bath temperature $\approx 160°$) for one hour and was cast onto 50 ml ice. A gummy solid which formed was collected by filtration and recrystallized from ethanol, yielding 1.3 g product, colorless needles.

A 408 mg portion of the N-toluenesulfonyl-4-nitro-2,6-dimethyl aniline was then dissolved in a mixture of 1 ml concentrated sulfuric acid and about 1.2 ml $H_2O$ and hydrolyzed to 4-nitro-2,6-dimethyl aniline by stirring at room temperature for about 16 hours. The reaction mixture was then cast onto a slush of 40 percent aqueous sodium hydroxide and ice and a fluorescent yellow-green powder which formed was collected by suction filtration, rinsed with water and air dried, yielding 188 mg product.

N-(2-chloroacetyl)-4-Nitro-2,6-dimethyl aniline was produced from 3.93 g 4-nitro-2,6-dimethyl aniline and a solution of 3.12 g chloroacetyl chloride in 13 ml dry benzene. The 4-nitro,2,6-dimethyl aniline was dissolved in 100 ml dry benzene (with heating, as required, to dissolve all of the solid). The chloroacetyl chloride solution was then added dropwise to the 4-nitro-2,6-dimethyl aniline solution A precipitate started forming almost immediately and, as reaction progressed, the bright yellow color faded and was replaced by a pale creme color. After one hour solids were filtered from the reaction mixture; the filter cake was washed with water and ethanol, and was air dried, yielding 5.0 g product, a fluffy, pale yellow powder.

To produce 4-nitro-monoethylgylcinexylidide ("4-nitro-MEGX") a 50 ml round bottomed flask equipped with a dry ice/acetone condenser was charged with 1.5 g N-(2-chloroacetyl)-4-Nitro-2,6-dimethyl aniline and 10 ml ethyl amine. The reaction mixture was stirred at room temperature for 1 hour, and was then concentrated by rotary evaporation. The crude product which resulted was dissolved in methylene chloride. The methylene chloride solution was washed twice with water and once with brine and was then dried on sodium sulfate. Solids were filtered from the dried solution, and the filtrate was subjected to rotary evaporation, which yielded 1.4 g crude product, a greenish oil.

Figure 5:
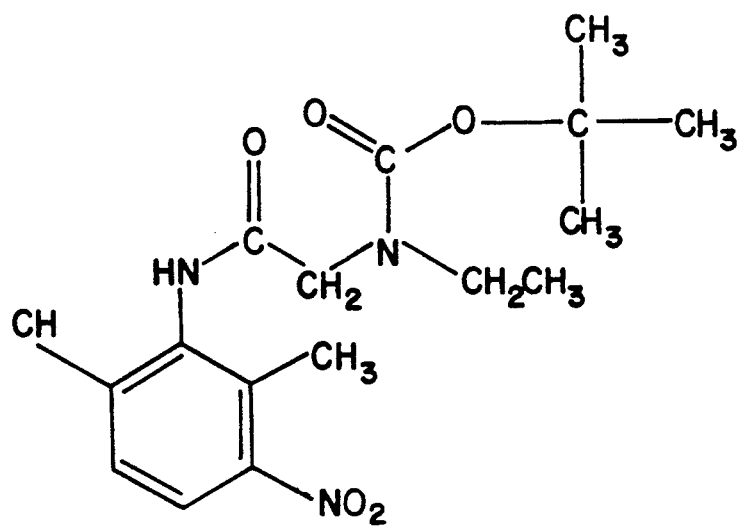

To produce N-t-BOC-4-nitro-monoethylglycinexylidide ("N-t-BOC-4-nitro-MEGX;" the compound is a position isomer of that shown in FIG. 5 of the attached drawings), a solution of 1.4 g crude 4-nitro-MEGX (the greenish oil produced as described in the preceding paragraph) in 10 ml dry dimethyl formamide was added to 0.986 g triethyl amine; the mixture was cooled to 0° on an ice bath; and an addition of 1.7 g di-tert-butyl dicarbonate was made. The reaction mixture was stirred for ten minutes, after which time the ice bath was removed and stirring was continued for another three hours. The reaction mixture was concentrated by high vacuum rotary evaporation, and the oil which remained was dissolved in 30 ml ethyl acetate. The ethyl acetate solution was washed with 30 ml 0.1N HCl, 30 ml water, and 30 ml brine and was then dried with sodium sulfate. Solids were filtered from the dried solution and solvent was removed from the filtrate by rotary evaporation, leaving a brown oil. The oil was purified by flash chromatography (silica-hexanes containing 40%/$_v$ ethyl acetate), yielding 1.94 g product, an off white solid.

A 1.5 g portion of the N-t-BOC-4-nitro-MEGX produced as described in the preceding paragraph was dissolved in 50 ml absolute ethanol and reduced to 4-amino-N-t-BOC-MEGX, using 100 mg platinum oxide as a catalyst. A solution of the N-t-BOC-4-nitro-MEGX in the ethanol and the platinum oxide were placed in a large Parr bottle. The bottle was alternately evacuated and then pressurized with hydrogen three times, and was then pressurized to 50 psig with hydrogen and placed on a shaker. The pressure was released after one hour of shaking, and the catalyst was filtered from the reaction mixture and washed with absolute ethanol. The ethanol filtrate from the catalyst washing was combined with the reaction mixture filtrate and the combined organic phase was concentrated by rotary evaporation, yielding 1.29 g product, a white foam.

The 4-amino-t-BOC-monoethylglycinexylidide can be dissolved in methylene chloride containing trifluoroacetic acid and stirred at room temperature to produce 4-amino-monoethylglycinexylidide. The reaction conditions and work-up described above for the preparation of 3-amino-monoethylglycinexylidide can be used.

Similarly, an MEGX tracer having the structure of FIG. 1 of the attached drawings where $Y^2$ is the moiety of FIG. 6 of the attached drawings, $Y^1$ is H and M is $CH_2NHCH_2CH_3$ can be produced from a solution of 6-carboxy fluorescein in dry dimethyl formamide, isobutyl chloroformate, triethyl amine and a solution of 4-amino-t-BOC-monoethylglycinexylidide dissolved in 125 μl dry dimethyl formamide. The reaction conditions and work-up described above in connection with the description of the preparation of a tracer having the structure of FIG. 1 of the attached drawings where $Y^1$ is the moiety of FIG. 6, $Y^2$ is H and M is $CH_2NHCH_2CH_3$ can be used.

Figure 4:
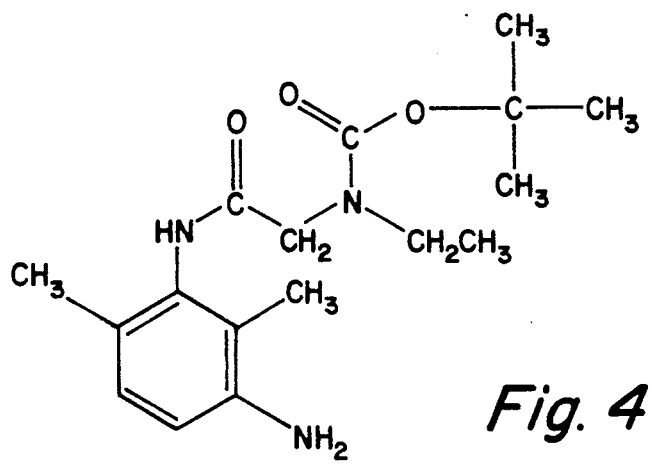
Figure 8:
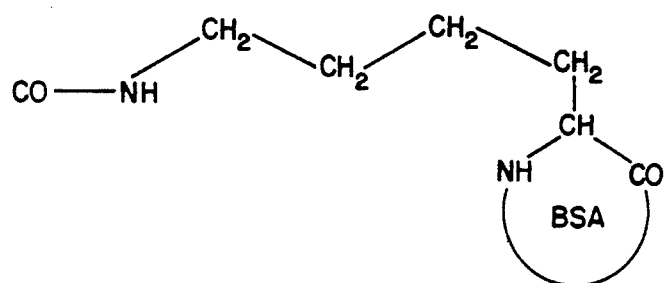
Figure 9:
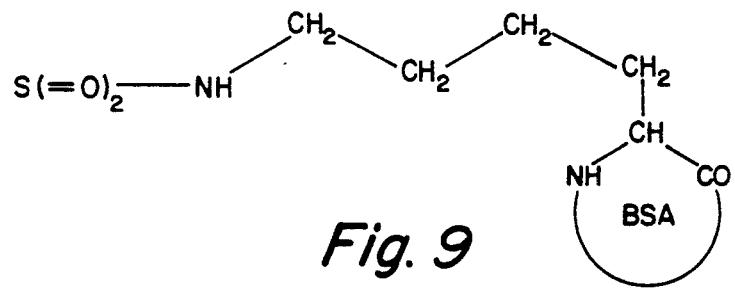
Figure 10:
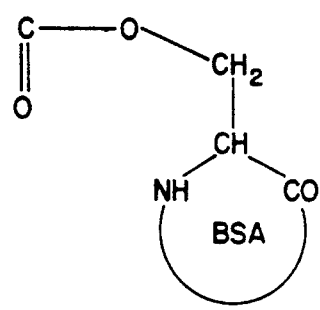

Other immunogens according to the invention can be produced by preparing a composition having the structure of FIG. 4 of the attached drawings, except that $NH_2$ is replaced by a moiety having the structure $C(=O)-OR$ where $C(=O)-OR$ is an active ester, or the position isomer thereof where $C(=O)-OR$ is in the 4-position, and reacting that composition with bovine serum albumin to produce, as a consequence of a major reaction with lysine $(NH_2CH_2CH_2CH_2CH_2CH(NH_2)COOH)$ on the bovine serum albumin and a minor reaction with serine $(CH_2OHCH(NH_2)COOH)$ on the bovine serum albumin, immunogens according to the invention having the structure, of FIG. 1 of the attached drawings where M is $CH_2NHCH_2CH_3$, one of $Y^1$ and $Y^2$ is H, and the other has the structure of FIGS. 8 and 10, respectively, of the attached drawings The active ester can be produced by reacting the corresponding carboxy compound with N-hydroxysuccinimide and N,N'-dicyclohexylcarbodiimide (see, for example, U.S. Pat. No. 4,668,640, column 8, lines 24 and following). Still other immunogens according to the invention can be produced by preparing a composition having the structure of FIG. 4 of the attached drawings, except that $NH_2$ is replaced by a moiety having the structure $S(=O)_2Cl$, or the position isomer thereof where $S(=O)_2Cl$ is in the 4- position, and reacting that composition with bovine serum albumin to produce, as a consequence of a major reaction with lysine $(NH_2CH_2CH_2CH_2CH_2CH(NH_2)COOH)$ on the bovine serum albumin and a minor reaction with serine $(CH_2OHCH(NH_2)COOH)$ on the bovine serum albumin, immunogens according to the invention having the structure of FIG. 1 of the drawings where M is $CH_2NHCH_2CH_3$, one of $Y^1$ and $Y^2$ is H, and the other has the structure of FIG. 9 of the attached drawings.

Still other immunogens according to the invention having the structure of FIG. 1 of the drawings where M is $CH_2CH_2CH_2CH_3$ can be produced by reacting 3-nitro-2,6-dimethyl aniline or 4-nitro-2,6-dimethyl aniline with valeryl chloride in the presence of pyridine (producing a compound having the structure of FIG. 1 where $Y^1$ or $Y^2$ is $NO_2$, the other is H and M is $CH_2CH_2CH_2CH_3$), reducing the $NO_2$ group to $NH_2$, diazotizing and coupling with bovine serum albumin, the last three steps as described above. In a like manner, immunogens according to the invention having the structure of FIG. 1 of the drawings where M is $CH_2OCH_2CH_3$ can be produced by reacting N-(2-chloroacetyl)-3-nitro-2,6-dimethyl aniline or N-(2-chloroacetyl)-4-nitro-2,6-dimethyl aniline with sodium ethoxide dissolved in ethyl alcohol (producing a compound having the structure of FIG. 1 where $Y^1$ or $Y^2$ is $NO_2$, the other is H and M is $CH_2OCH_2CH_3$), reducing the $NO_2$ group to $NH_2$, diazotizing and coupling with bovine serum albumin, the last three steps as described above.

Tracers according to the invention can also be produced by reacting a monoethylglycinexylidide having the structure of FIG. 1 where M is $CH_2NHCH_2CH_3$, one of $Y^1$ and $Y^2$ is COOH and the other is H, with a 4-aminomethylflourescein derivative produced as described in Example 2 of U.S. Pat. No. 4,614,823, Abbott Laboratories, or by reacting a monoethylglycinexylidide having the structure of FIG. 1 where M is $CH_2NHCH_2CH_3$, one of $Y^1$ and $Y^2$ is $NH_2$ and the other is H with a position isomer of the 6-carboxy fluorescein used as described above or an active ester thereof. Position isomers of 6-carboxy fluorescein are disclosed in U.S. Pat. No. 4,668,640, Abbott Laboratories.

Still other immunogens according to the invention can be produced by substituting for the bovine serum albumin used in the procedures described above which produce immunogens, equivalent amounts of hemocyanin, thyroglobulin, ovalbumin, immunoglobulins or of a synthetic protein, e.g., polylysine.

The MEGX tracer and the MEGX antibody produced by the immunogen, as described above in Example 1, were used, respectively, as a tracer and as an antibody in fluorescence polarization immunoassays conducted as follows:

(1) a measured volume of a standard or test serum was delivered into a test tube and diluted with a buffer;

(2) a known concentration of an antibody of the instant invention was then added to each tube;

(3) a known concentration of a tracer of the instant invention was added to the tubes;

(4) the reaction mixture was incubated at 35°; and (5) the amount of tracer bound to antibody was measured by fluorescence polarization techniques as a measure of the amount of MEGX in the sample.

The following materials were used in carrying out the immunoassays:

1. The MEGX tracer produced as described above in an aqueous system containing 0.96 percent of citric acid, 5.0 percent of 5-sulfo-salicylate and 0.1 percent of sodium azide.

2. The MEGX antibody produced as described above in 0.1 M phosphate buffer containing 2.0 percent ethylene glycol.

3. Pretreatment solution consisting of a buffer (pH 7.4) which is commercially available under the trade designation "TABS" containing 0.1 percent of lithium-3,5-diiodosalicylate and 0.1 percent of sodium azid.

4. Samples of human serum or urine containing MEGX.

5 Cuvettes, 10×50 mm glass flat bottom tubes used as cuvettes.

6. Fluorometer capable of measuring fluorescence polarization with a precision of ±0.01 unit.

The assay method involved the following steps:

1. A 5.0 μl sample was pipetted into a cuvette container with 25 μl MEGX antibody and 12.5 μl of pretreatment solution. The volume of the solution in the cuvette was diluted to approximately 955 μl with phosphate buffer containing 0.01 percent of bovine gamma-globulin ("BGG").

2. The contents of the cuvette were mixed well. After three minutes, a background determination of fluorescence polarization was made.

3. An additional 5 μl portion of the sample was pipetted into the cuvette. The volume of the solution in the cuvette was diluted to approximately 1500 μl with phosphate buffer containing 0.01 percent of BGG.

4. The contents in the cuvette were mixed well and allowed to incubate for approximately 1 minute, after which additions of 12.5 μl of pretreatment solution and of 25.0 μl of MEGX tracer were pipetted into the cuvette. The solution in the cuvette was diluted with phosphate buffer containing 0.01 percent of BGG to bring the total volume to approximately 2000 μl.

5. The contents of the cuvette were mixed well and allowed to incubate for three minutes at 35°.

6. The fluorescence polarization value of the composition in the cuvette was then determined using an appropriate instrument (fluorometer).

The results of a series of serum standards containing MEGX at concentrations between 0 and 250 ng/ml are set forth below:

| Concentration of MEGX in ng/ml | Approximate Polarization |
|---|---|
| 0.00 | 179.03 |
| 25.00 | 156.99 |
| 75.00 | 125.75 |
| 125.00 | 107.93 |
| 175.00 | 96.58 |
| 250.00 | 86.97 |

It has been found that tracers according to the instant invention and alcohol solutions thereof are unstable to the extent that they must be prepared and purified just before they are used to carry out an immunoassay, but that aqueous solutions thereof buffered to a pH in the range of about 1.5 to about 2.1 can be stored for substantial periods of time. The tracer solution identified above, composed of an MEGX tracer in an aqueous system containing 0.96 percent of citric acid, 5.0 percent of 5-sulfo-salicylate and 0.1 percent of sodium azide, is an example of a stable aqueous tracer solution.

While preferred embodiments of the invention have been described, it will be appreciated that various changes and modifications can be made without departing from the spirit and scope of the invention as defined in the attached claims.

We claim:

1. A substituted monoethylglycinexylidide or analogue having the structure

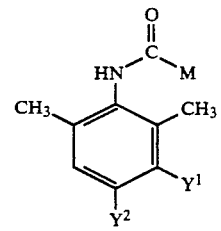

wherein M is $CH_2NHCH_2CH_3$, $CH_2CH_2CH_2CH_3$ or $CH_2OCH_2CH_3$, one of $Y^1$ and $Y^2$ is H and the other is selected from the group consisting of the residue of a trizinyl amino fluorescein, the residue of an amino methyl fluorescein and the residue of a substituted carboxyfluorescein chemically bonded to the glycinexylidide or analogue moiety.

2. A substituted monoethylglycinexylidide or analogue as claimed in claim 1 wherein $Y^1$ is hydrogen and $Y^2$ is a fluorescein moiety having the structure 3. A substituted monoethylglycinexylidide or analogue as claimed in claim 1 wherein $Y^2$ is hydrogen and $Y^1$ is a fluorescein moiety having the structure
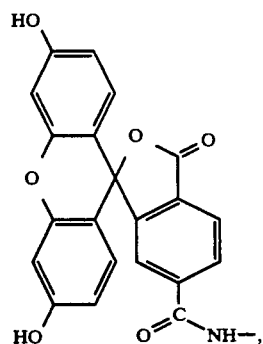
4. The substituted monoethylglyeinexylidide or analogue of claim 1 dissolved to form an aqueous solution which is buffered to a pH between about 1.5 and 2.1.
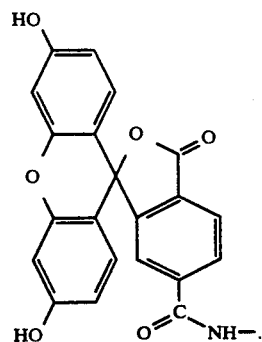
* * * * *